(12) United States Patent
Huculak et al.

(10) Patent No.: US 11,738,154 B2
(45) Date of Patent: Aug. 29, 2023

(54) MICRO-VOLUME INJECTORS WITH DOSE GUIDANCE AND METHODS FOR USE

(71) Applicant: ALTAVIZ, LLC, Irvine, CA (US)

(72) Inventors: John C. Huculak, Mission Viejo, CA (US); Jack R. Auld, Laguna Niguel, CA (US); Hien Nguyen, Westminster, CA (US); Tammo Heeren, Aliso Viejo, CA (US); Matthew McCawley, San Clemente, CA (US); Eric Anderfaas, Westminster, CA (US); John C. Dunne, Jr., Costa Mesa, CA (US)

(73) Assignee: ALTAVIZ, LLC, Irvine, CA (US)

( * ) Notice: Subject to any disclaimer, the term of this patent is extended or adjusted under 35 U.S.C. 154(b) by 256 days.

(21) Appl. No.: 17/019,133

(22) Filed: Sep. 11, 2020

(65) Prior Publication Data

US 2021/0069426 A1    Mar. 11, 2021

Related U.S. Application Data

(60) Provisional application No. 63/003,117, filed on Mar. 31, 2020, provisional application No. 62/899,058, filed on Sep. 11, 2019.

(51) Int. Cl.
*A61M 5/315* (2006.01)
*A61M 5/24* (2006.01)
(Continued)

(52) U.S. Cl.
CPC ....... *A61M 5/31568* (2013.01); *A61F 9/0008* (2013.01); *A61M 5/24* (2013.01);
(Continued)

(58) Field of Classification Search
CPC .... A61M 5/31568; A61M 5/281; A61M 5/24; A61M 5/31581; A61M 5/3157; A61M 2205/3306; A61M 2205/52
See application file for complete search history.

(56) References Cited

U.S. PATENT DOCUMENTS

| | | | |
|---|---|---|---|
| 2016/0339178 A1 | 11/2016 | Baker et al. | |
| 2017/0312422 A1* | 11/2017 | Auld | A61M 5/2053 |
| 2020/0114088 A1* | 4/2020 | Schabbach | A61M 5/2422 |

FOREIGN PATENT DOCUMENTS

| | | | | |
|---|---|---|---|---|
| EP | 2537546 A1 | 12/2012 | | |
| WO | WO-2012175503 A1 * | 12/2012 | | A61M 5/1452 |

OTHER PUBLICATIONS

Heo, Joo Hyung, Korean Intellectual Property Office, International Search Report and Written Opinion for corresponding International Application No. PCT/US2020/050573, dated Jan. 4, 2021, 14 pages.

* cited by examiner

*Primary Examiner* — Tasnim Mehjabin Ahmed
(74) *Attorney, Agent, or Firm* — William A. English; Vista IP Law Group LLP

(57) ABSTRACT

Injector devices and methods for using them to deliver medicament into a patient's body, e.g., sub-retinally within an eye, are provided. The injector includes a cartridge including a piston slidably disposed within an interior for delivering medicament within the interior through an outlet, and a driver including a plunger coupled to the piston, a source of pressurized fluid, and an actuator member for opening a flow path at least partially between the source and the plunger to advance the plunger and piston to deliver medicament from the interior. One or more sensors are operatively coupled to the plunger to measure displacement of the plunger, a processor is coupled to the sensor(s) for analyzing sensor signals to measure volume of medicament delivered from the interior, and an output device, e.g., one or more LEDs or speakers, provide outputs related to the volume of medicament delivered.

26 Claims, 6 Drawing Sheets

(51) Int. Cl.
*A61M 5/28* (2006.01)
*A61F 9/00* (2006.01)

(52) U.S. Cl.
CPC .......... *A61M 5/281* (2013.01); *A61M 5/3157* (2013.01); *A61M 5/31581* (2013.01); *A61M 2205/3306* (2013.01); *A61M 2205/3317* (2013.01); *A61M 2205/3368* (2013.01); *A61M 2205/3584* (2013.01); *A61M 2205/502* (2013.01); *A61M 2205/52* (2013.01); *A61M 2205/581* (2013.01); *A61M 2205/584* (2013.01); *A61M 2205/587* (2013.01)

MICRO-VOLUME INJECTORS WITH DOSE GUIDANCE AND METHODS FOR USE

RELATED APPLICATION DATA

The present application claims benefit of provisional application Ser. No. 62/899,058, filed Sep. 11, 2019, and 63/003,117, filed Mar. 31, 2020, the entire disclosures of which are expressly incorporated by reference herein.

FIELD OF THE INVENTION

The present invention relates to devices and methods for delivering agents into a patient's body and, more particularly, to injectors for delivering precise doses of agents, e.g., gene vectors and/or stem cells sub-retinally within a patient's eye, and to systems and methods for using such injectors.

BACKGROUND

There are many applications where controlled delivery of a medicament is desired while maintaining precise position control of the delivery needle to deliver a precise volume of fluid in a precise location. For example, syringe devices may be used for sub-retinal injections in the treatment of several disease conditions of an eye.

Such sub-retinal injections involve many complications. For example, positioning the tip of a syringe cannula precisely within the eye can be difficult, particularly for identifying when the tip is through the retina layer. Further, forming a bleb (i.e., the bolus of fluid delivered subretinally) risks breaks or tears in the retina.

In addition, such current procedures typically require two surgeons, a primary surgeon to position the cannula tip close to the retina, and an assistant surgeon to push the syringe plunger rod as the primary surgeon advances the tip towards the retina. The assistant surgeon attempts to note the plunger position at bleb start and calculate, in real time, the volume of fluid being delivered to determine when a target dose is achieved. Thus, current procedures are complicated and it is difficult to know when a target dose has been delivered.

Therefore, devices and methods for that facilitate delivering fluids into a patient's body would be useful.

SUMMARY

The present invention is directed to devices and methods for delivering agents into a patient's body and, more particularly, to injectors for delivering precise doses of agents, e.g., gene vectors and/or stem cells sub-retinally within a patient's eye, and to systems and methods for using such injectors.

In accordance with an exemplary embodiment, a device is provided for delivering a medicament into a patient's body that includes a syringe cartridge comprising a housing including a proximal end, a distal end, and defining an interior, the cartridge further comprising a piston slidably disposed within the interior for delivering a medicament within the interior through an outlet in the distal end; a syringe driver comprising a plunger for advancing the piston within the interior of the housing, a source of pressurized fluid, and an actuator member for opening a flow path at least partially between the source and the plunger to advance the plunger and piston to deliver medicament from the interior of the housing; one or more sensors operatively coupled to the plunger to measure displacement of the plunger, e.g., axially within the driver; a processor coupled to the one or more sensors for analyzing signals from the one or more sensors to determine volume of medicament delivered from the outlet; and an output device coupled to the processor for providing one or more outputs related to the volume of medicament delivered from the outlet.

In accordance with another embodiment, an injector device is provided for delivering a medicament into a patient's body that includes a syringe cartridge including a housing defining an interior, the cartridge further including a piston slidably disposed within the interior for delivering a medicament within the interior through an outlet of the housing; a syringe driver including a plunger for advancing the piston within the interior of the housing, a source of pressurized fluid, and an actuator member for opening a flow path at least partially between the source and the plunger to advance the plunger and piston to deliver medicament from the interior of the housing; one or more sensors operatively coupled to the plunger to measure displacement of the plunger within the interior; a processor coupled to the one or more sensors for analyzing signals from the one or more sensors to measure medicament delivered from the outlet, e.g., measure volume based at least in part on the displacement of the plunger; a start actuator coupled to the processor; and one or more light sources coupled to the processor, the processor configured to activate the one or more light sources to: a) emit a first color when the actuator member is initially actuated to begin delivering medicament from the cartridge, b) emit a second color when the processor detects that the start actuator has been actuated to indicate when medicament is being delivered to a target location, at which time the processor begins to measure the volume of medicament being delivered to the target location based at least in part on the signals, and c) emit a third color when the processor confirms that a predetermined dose of the medicament has been delivered to the target location.

In accordance with still another embodiment, a system is provided for delivering a medicament into a patient's body that includes an injector device comprising a) a syringe cartridge comprising a housing defining an interior and a piston slidably disposed within the interior for delivering medicament within the interior through a distal outlet of the housing; a syringe driver comprising a plunger coupled to the piston, a driver module, and an actuator member for delivering pressurized fluid within the driver module to advance the plunger and piston to deliver medicament from the interior of the housing; one or more sensors operatively coupled to the plunger to measure displacement of the plunger within the interior; a processor coupled to the one or more sensors for analyzing signals from the one or more sensors to measure volume of medicament delivered from the outlet, e.g., based at least in part on the displacement of the plunger; one or more output devices coupled to the processor for providing one or more outputs related to the volume of medicament delivered from the outlet and an injector communication interface. In addition, the system includes an electronic device including a device communication interface for transmitting signals to and receiving signals from the injector communication interface; a user interface for entering a "start" signal for transmission to the processor, whereupon the processor analyzes signals from the one or more sensors to measure the volume of medicament delivered; and a display for presenting an indicator field including information regarding the volume of medicament delivered from the outlet received in signals from the processor.

In an exemplary embodiment, the one or more output devices include one or more light sources coupled to the processor, the processor configured to activate the one or more light sources to emit a first color when the actuator member is initially actuated to begin delivering medicament from the cartridge, emit a second color when the processor detects that the start actuator has been actuated to indicate when medicament is being delivered to a target location, at which time the processor begins to measure the volume of medicament being delivered to the target location based at least in part on the signals, and emit a third color when the processor confirms that a predetermined dose of the medicament has been delivered to the target location.

In accordance with another embodiment, a method is provided for delivering a medicament into a patient's body providing or loading a volume of medicament into an interior of a syringe cartridge comprising a piston slidably disposed within the interior and a cannula; coupling the syringe cartridge to a driver, thereby coupling a plunger of the driver to the piston; inserting the cannula into the patient's body; activating an actuator of the driver to advance the plunger, thereby advancing the piston to deliver medicament from the interior into the patient's body whereupon one or more sensors measure displacement of the plunger, signals from the one or more sensors are analyzed to measure volume of medicament delivered from the cannula based at least in part on the signals, and an output is provided related to the volume of medicament delivered.

In one embodiment, the output includes a light source emitting a first color when the actuator member is initially actuated to provide a visual indication that medicament is being delivered from the cartridge. Optionally, the method may also include positioning the cannula at a target location; and actuating a start actuator on the driver to indicate that medicament is being delivered to a target location, at which time the signals from the one or more sensors are analyzed to measure the volume of medicament being delivered to the target location, the light source emitting a second color to provide visual indication that the medicament is being delivered to the target location. Optionally, the light source may emit a third color when a predetermined dose of the medicament has been delivered to the target location to provide a visual indication that the dose has been delivered.

In accordance with yet another embodiment, a method is provided for delivering a medicament into a patient's body that includes loading a volume of medicament into an interior of a syringe cartridge comprising a piston slidably disposed within the interior and a cannula; coupling the syringe cartridge to a driver, thereby coupling a plunger of the driver to the piston; inserting the cannula into the patient's body; activating an actuator of the driver to advance the plunger, thereby advancing the piston to deliver medicament from the interior into the patient's body whereupon one or more sensors measure displacement of the plunger, signals from the one or more sensors are analyzed to measure volume of medicament delivered from the cannula based at least in part on the signals, and a light source emits a first color when the actuator member is initially actuated to provide a visual indication that medicament is being delivered from the cartridge; positioning the cannula at a target location; and actuating a start actuator on the driver to indicate that medicament is being delivered to a target location, at which time the signals from the one or more sensors are analyzed to measure the volume of medicament being delivered to the target location, the light source emitting a second color to provide visual indication that the medicament is being delivered to the target location.

In accordance with another embodiment, a method is provided for delivering a medicament into a patient's body that includes loading a volume of medicament into an interior of a syringe cartridge comprising a piston slidably disposed within the interior and a cannula; coupling the syringe cartridge to a driver, thereby coupling a plunger of the driver to the piston; inserting the cannula into the patient's body; activating an actuator of the driver to advance the plunger, thereby advancing the piston to deliver medicament from the interior into the patient's body whereupon one or more sensors measure displacement of the plunger, signals from the one or more sensors are analyzed to monitor volume of medicament delivered from the cannula based at least in part on the signals, and an output is provided related to the volume of medicament delivered.

In accordance with still another embodiment, a method is provided for delivering a medicament sub-retinally within a patient's eye that includes loading a volume of medicament into an interior of a syringe cartridge comprising a piston slidably disposed within the interior and a cannula; coupling the syringe cartridge to a driver, thereby coupling a plunger of the driver to the piston; inserting the cannula into the patient's eye such that the cannula is disposed adjacent the patient's retina; activating an actuator of the driver to advance the plunger, thereby advancing the piston to deliver medicament from the interior into the patient's eye whereupon one or more sensors measure displacement of the plunger, a processor analyzes signals from the one or more sensors to monitor volume of medicament delivered from the cannula based at least in part on the signals, and an output is provided related to the volume of medicament delivered. The method may also include advancing the cannula through the retina while continuing to deliver medicament; and activating an activation device when the retina is pierced whereupon the activation device communicates a start signal to the processor and the processor continues to analyze signals from the one or more sensors to monitor volume of medicament delivered sub-retinally.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It is emphasized that, according to common practice, the various features and design elements of the drawings are not to-scale. On the contrary, the dimensions of the various features and design elements are arbitrarily expanded or reduced for clarity. Included in the drawings are the following figures.

DETAILED DESCRIPTION OF THE EXEMPLARY EMBODIMENTS

Figure 1:
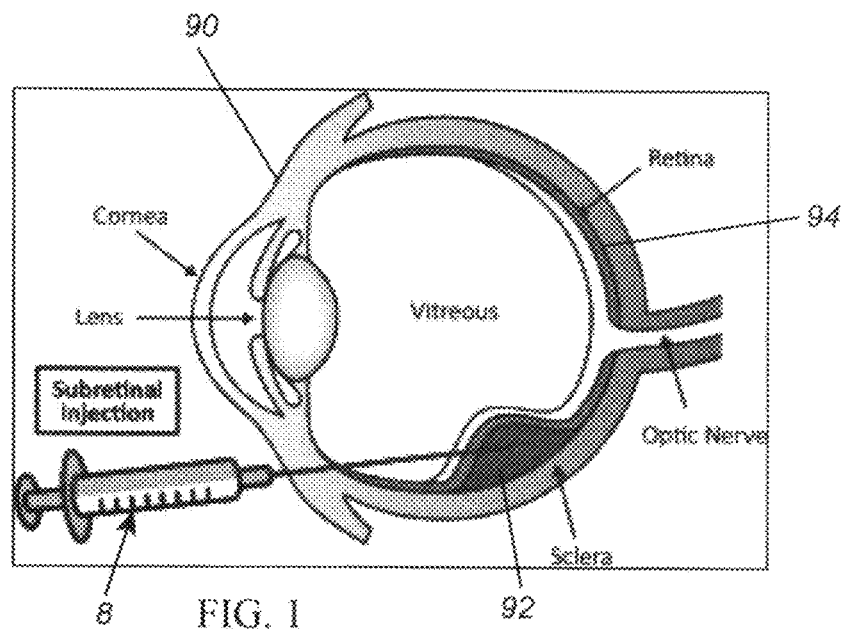
FIG. 1 is an enlarged cross-sectional view of a human eye showing administration of a sub-retinal injection to the eye using a syringe device.

Before the exemplary embodiments are described, it is to be understood that the invention is not limited to particular embodiments described, as such may, of course, vary. The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary, or the following detailed description. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described.

It must be noted that as used herein and in the appended claims, the singular forms "a," "an," and "the" include plural referents unless the context clearly dictates otherwise. Thus, for example, reference to "a compound" includes a plurality of such compounds and reference to "the polymer" includes reference to one or more polymers and equivalents thereof known to those skilled in the art, and so forth.

There are many applications where controlled delivery of a medicament is desired while maintaining precise position control of the delivery needle and/or monitoring delivery to confirm that a desired volume of fluid has been delivered. The devices and methods described herein may facilitate precise delivery of medicaments into a patient's body, e.g., one or more viscous fluids or other flowable material for various therapeutic and/or diagnostic purposes. As used herein, "medicament" is intended to refer to any such fluids, agents, or materials, such as those described herein. For example, below is a summary of exemplary applications where the devices and methods described herein may be used to deliver fluids into a patient's body.

Ophthalmology: As shown in FIG. 1, a syringe device 8 may be used for sub-retinal injections in the treatment of several disease conditions of an eye 90. The syringe device 8 may include a syringe cartridge and a syringe driver (not shown), similar to any of the embodiments described herein.

Treatment of retinal vein occlusions: Multiple indications may be treated by the administration of therapeutic agents into the sub-retinal space 92 in the eye 90, e.g., as shown in FIG. 1. In cases of branch retinal vein occlusion (BRVO) and central retinal vein occlusion (CRVO), 50 to 150 µL of tissue plasminogen activator (TPA) may be administered through relatively small hypodermic needles (e.g., not more than 41 gauge) to dissolve blood clots formed by sub-retinal hemorrhages during the course of retinal surgery. In these cases, the ophthalmic surgeon may place the tip under the surface of a patient's retina and slowly inject the TPA to create a bleb of medicament that dissolves the coagulated blood over the course of a few days.

Gene therapy for the treatment of macular degeneration: Age-related macular degeneration (AMD) is a leading cause of vision loss and blindness among the elderly. AMD is a progressive ocular disease of the part of the retina, called the macula, which enables people to read, visualize faces, and drive. The disease initially causes distortion in central vision, and eventually leads to legal blindness. A layer of cells at the back of the eye, called the retinal pigment epithelium (RPE), provides support, protection, and nutrition to the light sensitive cells of the retina, i.e., the photoreceptors consisting of rods and cones. The dysfunction and/or loss of these RPE cells play a critical role in the loss of the photoreceptors and hence blindness in AMD. Recent advances in research show promise in new therapies to treat AMD. Human embryonic stem cells, gene therapies, complement factors, and viral vectors are under development with early stage animal studies and/or clinical trials. Some of these treatments require administration of the cells into targeted areas of the eye including the sub-retinal space or the suprachoroidal space with exquisite control over position, volumetric delivery rate, and/or total volume.

Dermal fillers and botulinum toxins for use in cosmetic procedures: In dermal filler procedures, high viscosity purified fluids or gels are injected into various parts of the anatomy to replace subcutaneous fat that has diminished through aging and enhance the volume and fullness of the features, particularly in lips, chins, nasolabial folds, tear troughs, and cheeks. In other procedures, botulinum toxin is injected into the glabella, forehead and orbicularis regions to neutralize the muscles to provide relaxation and to reduce wrinkles in those regions of the face. In all of these procedures, the ability to have exquisite control over flowrate, inject highly viscous fluids repeatably in tissues with varying resistance would improve the consistency during the injections and tracking the volumes injected would enable consistent results over repeated treatments.

Figure 2A:
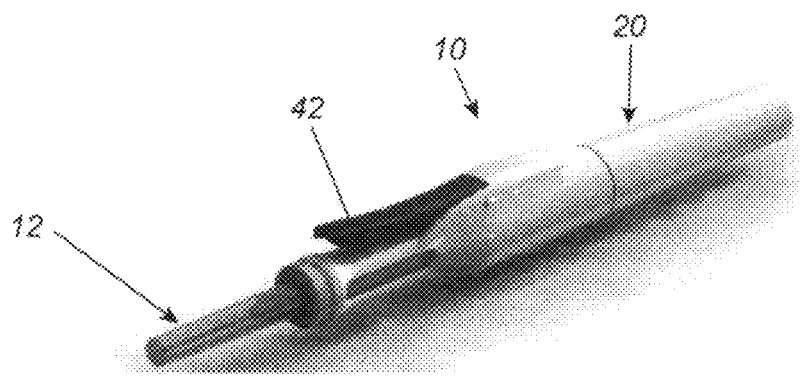
FIG. 2A is a perspective view of an exemplary embodiment of an injector including a driver and a syringe cartridge coupled to the driver for delivering a medicament from the syringe cartridge into a patient's body.
Figure 2B:
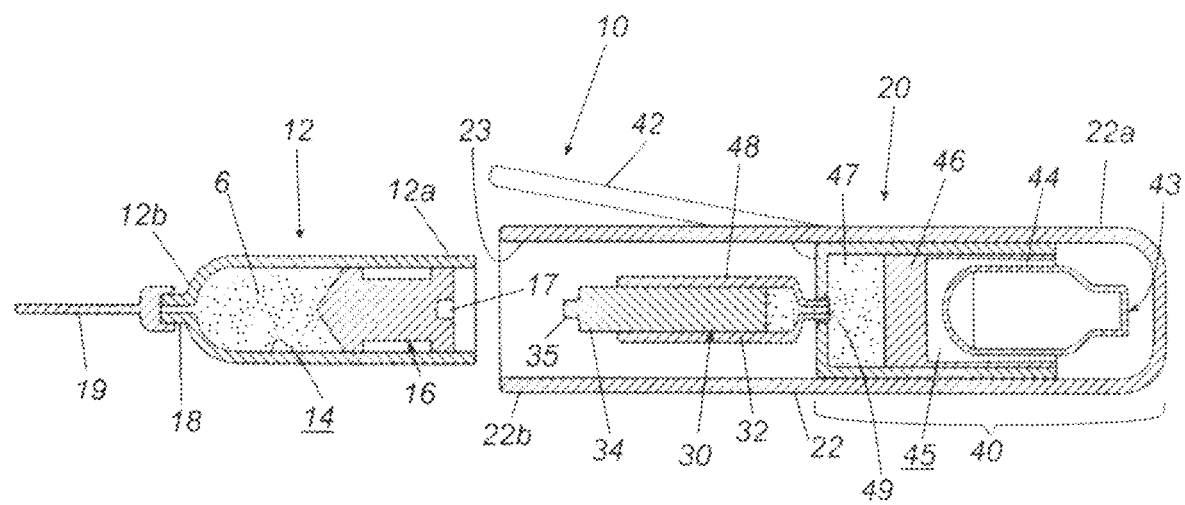
FIG. 2B is a cross-sectional view of the injector of FIG. 2A.
Figure 2C:
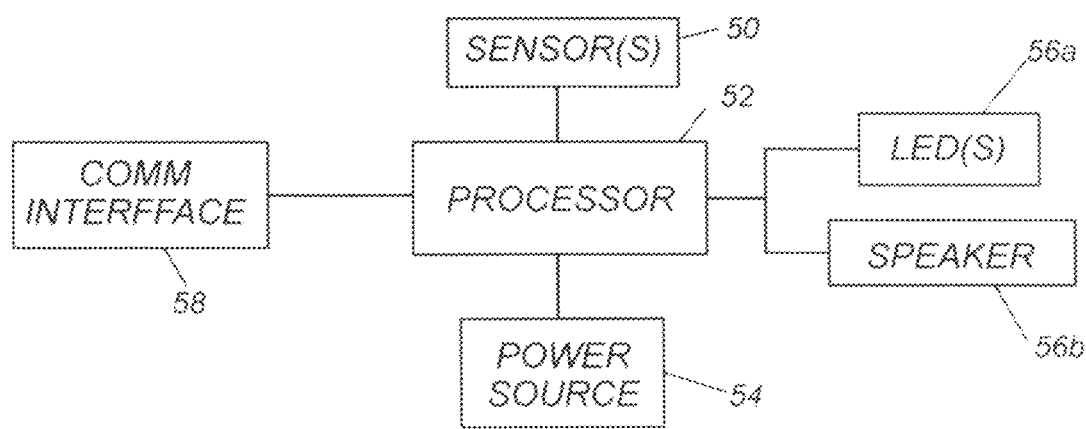
FIG. 2C is a schematic showing electronic components of the injector of FIGS. 2A and 2B.

Turning to FIGS. 2A-2C, an exemplary injector device 10 is shown for delivering a medicament 6 into a patient's body that includes a syringe cartridge 12 including a cartridge housing including proximal and distal ends 12a, 12b and defining an interior 14 and a piston 16 slidably disposed within the interior 14 for delivering medicament 6 within the interior 14 through an outlet or port 18 and/or needle cannula 19 on the distal end 12b of the cartridge 12, and a syringe driver 20 including a housing 22 containing a plunger 30 for advancing the piston 16 within the interior 14 of the cartridge 12 and a drive module 40. The proximal end 12a of the syringe cartridge 12 may be sized to be received within a distal region 23 of the driver housing 22 or otherwise removably coupled to a distal end 22b of the housing 22 such that the plunger 30 may be coupled to the piston 16 and advanced into the interior 14 of the cartridge 12 to deliver the medicament 6 through the port 18 and cannula 19. For example, the proximal end 12a of the cartridge 12 and the housing 22 may include one or more cooperating connectors (not shown) to secure the cartridge 12 to the housing 22 once inserted into the distal region 23, e.g., such that the port 18 (and the needle or cannula 19 connected to the port 18) extend distally from the housing 22. When the cartridge 12 is fully seated, the piston 16 may be coupled to the plunger 30, e.g., using one or more cooperating connectors 17, 35, such that distal advancement of the plunger 30 advances the piston 16 within the interior 14.

Thus, a desired volume of medicament 6 may be loaded or otherwise provided in interior 14 of the cartridge 12, which may then be coupled to the driver 20 immediately before injection, e.g., as described further elsewhere herein. A needle or cannula 19 may be removably connected to or permanently integrated into the port 18. Alternatively, the cartridge may be permanently integrated into the driver housing, e.g., to provide an inseparable, e.g., single-use disposable, device.

Figure 3:
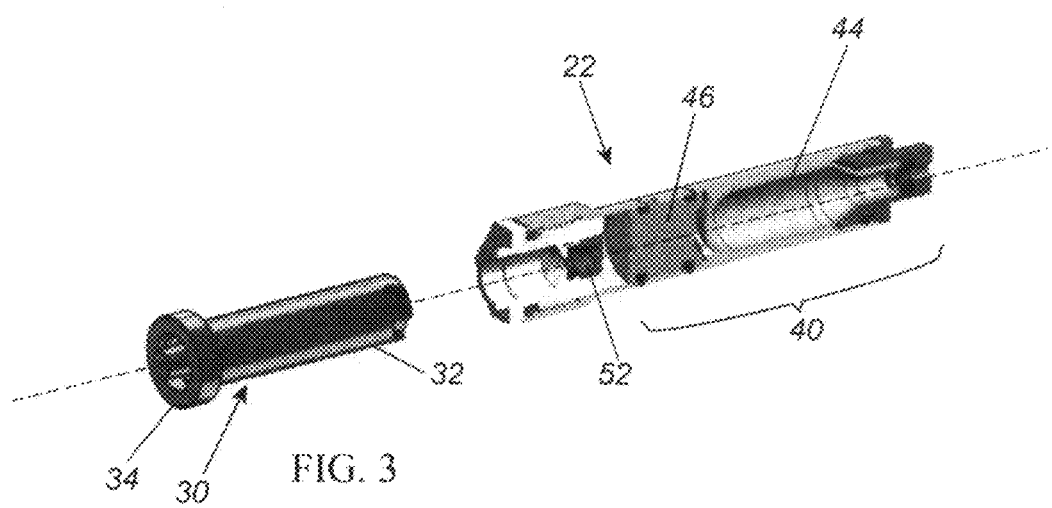
FIG. 3 is a cross-sectional view of an exemplary driver of the injector of FIGS. 2A-2C including a plunger slidable within a driver housing for delivering the medicament from the syringe cartridge.

As best seen in FIGS. 2B and 3, the driver 20 includes an outer housing 22 containing a driver module 40, e.g., including a source of pressurized fluid and/or other energy source 44, hydraulic fluid, and a lever or other actuator member 42 for opening one or more flow paths at least partially between the source 44 and the plunger 30 to advance the plunger 30 to deliver medicament from the cartridge 12. For example, as shown in FIG. 2B, a canister of pressurized gas or other high delivery force energy storage device 44 may be provided, e.g., within a proximal end 22a of the housing 22, which may be opened by a pin 43 during initial activation of the injector 10 to deliver pressurized gas into gas chamber 45, which may apply a distal force to a fluid piston 46. An incompressible fluid, e.g., silicone fluid, may be provided within fluid chamber 47 beyond the fluid piston 46 that communicates with an interior of plunger chamber 48 such that, upon actuation of the lever 42, the fluid may enter the plunger chamber 48 and advance the plunger 30 distally. In an exemplary embodiment, a needle valve (not shown) may be provided that includes a needle coupled to the lever 42, e.g., by a carriage (not shown) within the housing 122, which may be displaced when the lever 42 is actuated to open an orifice communicating between the fluid chamber 47 and the plunger housing 48, e.g., such that the fluid flows at a substantially consistent rate to displace the plunger 130 at a desired speed, as described further elsewhere herein. Additional information regarding exemplary embodiments of driver modules that may be included in the driver 20 are disclosed in U.S. Publication Nos. 2017/0258583, 2017/0312422, and 2019/0167,906, the entire disclosures of which are expressly incorporated by reference herein.

Figure 4:
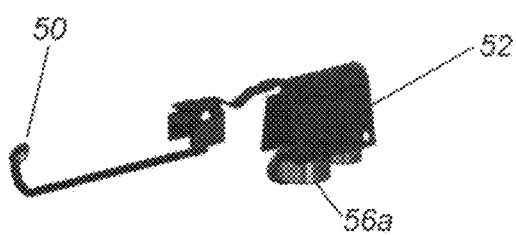
FIG. 4 shows an exemplary embodiment of the electronic components that may be provided within the driver housing of FIG. 3, e.g., including one or more optical sensors coupled to a processor and a multiple-color LED.

With additional reference to FIGS. 2C and 4, the driver 20 also includes one or more electronic components, e.g., one or more sensors 50 operatively coupled to the plunger 30 to measure displacement of the plunger 30 within the housing 22, a processor 52 coupled to the sensor(s) 50 for processing and/or analyzing signals from the sensor(s) 50 to determine a volume of medicament delivered from the port 18 based at least in part on the signals, one or more batteries or other power source 54, and one or more output devices, e.g., one or more LEDs 56a and/or speakers 56b, e.g. coupled to the processor 52 for providing one or more outputs related to the medicament delivered from the syringe cartridge 12, e.g., volume, flow rate, and/or other parameters, as described elsewhere herein. In the exemplary embodiment shown, one or more optical sensors 50 may be mounted within the housing 22 adjacent, e.g., concentrically around, the plunger 30 that may be coupled to the processor 52, e.g., including a linear quadrature decoder and/or other hardware or software components, to correlate linear displacement of the plunger 30 within the housing 22 to a volume of medicament delivered from the syringe cartridge 12 into the patient.

The processor 52 may monitor one or more delivery parameters, e.g., volume of fluid injected, during delivery of the medicament based on signals from the sensor(s) 50 and activate the output device(s) 56, e.g., to communicate information to the user and/or otherwise facilitate delivery. For example, one or more LEDs or other light sources 56a, e.g., a multiple-color LED or multiple LEDs of different colors, may be provided that be activated to provide visible indications related to the activation and/or operation of the injector 10, e.g., as described elsewhere herein. In addition or alternatively, the output device may include a speaker or other sound generator 56b that may generate audible signals in addition to or instead of the light source 56a.

Optionally, the processor 52 may include a clock (not shown), e.g., to measure time events and/or add time stamps to data stored or communicated by the processor 52. For example, the injector 10 may include on-board memory (not shown) that communicates with the processor 52 for storing data from signals from the sensor(s) 50, volume or other information determined by the processor 52 from the signals, such as total volume delivered, rate of delivery, dosing profile information, time of delivery, time between different events, such as between loading of the cartridge and delivery, and the like. In another option, the injector 10 include a temperature sensor (not shown) communicating with the processor 52 for monitoring temperature of the medicament.

In addition, the injector 10 may include a communication interface 58, e.g., a wireless interface including one or more antennas (not shown) configured to transmit and/or receive signals using Bluetooth or other RF communication protocols. For example, an external switch or activation device (not shown) may be provided that may communicate with the injector 10, e.g., via its own wireless communication interface, which may be used to communicate instructions or other information to the processor 52 and/or receive data or other information from the processor 52. In one embodiment, the activation device may simply be a switch that may be activated manually by an operator, e.g., a surgeon or assistant, whereupon the activation device may communicate a "start" signal to the processor 52 via the communications interface 58, such that the processor 52 monitors signals from the sensor(s) 50 to measure volume being delivered from the cartridge 12 based on the displacement of the plunger 30, e.g., to measure a dose or "bleb" delivered to a target region, as described elsewhere herein.

Figure 5B:
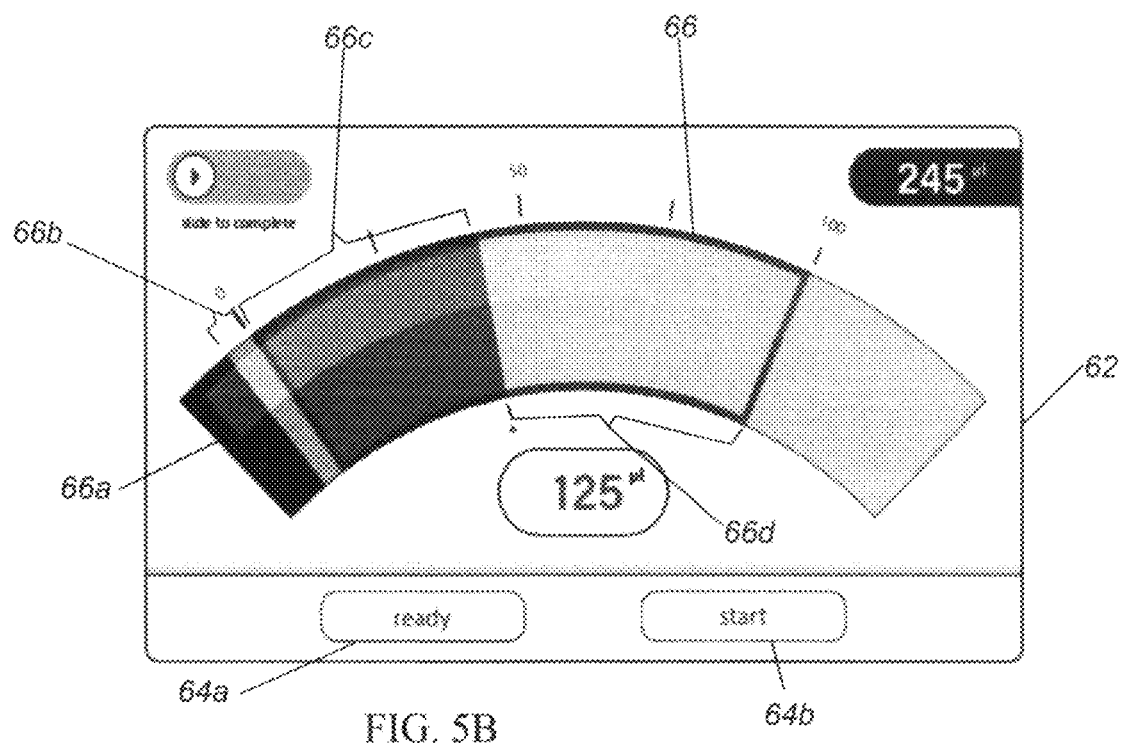
FIG. 5B shows an exemplary display that may be presented on the electronic device communicating with the injector shown in FIG. 5A.
Figure 5A:
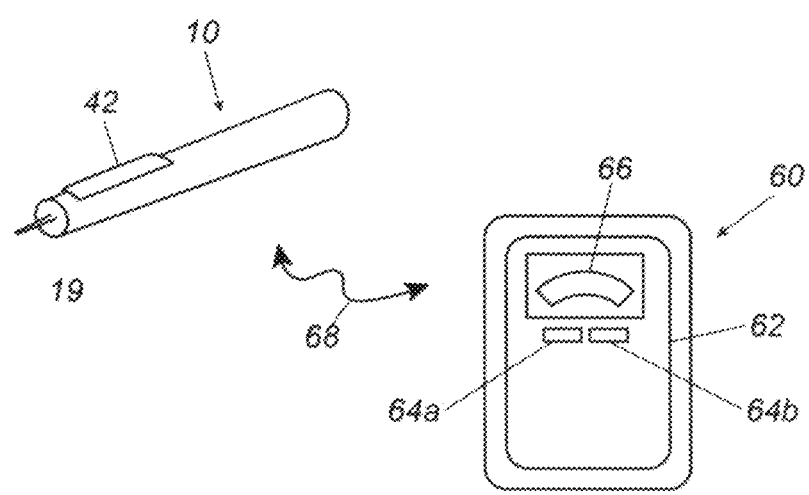
FIG. 5A shows a portable electronic device communicating with an injector, such as the injector of FIGS. 2A-2C.

Alternatively, as shown in FIGS. 5A and 5B, the activation device may be a wireless electronic device 60, e.g., a cellphone, tablet, and the like (not shown) that may provide a user interface to enable the operator to communicate the start signal, e.g., by pressing a "Start" icon 64b on a display 62 of the electronic device, e.g., as shown in FIG. 5B.

In this alternative, the electronic device 60 may provide additional functionality to facilitate use of the injector 10. For example, a "ready" icon 64a may be provided on the display 62, which may be selected whereupon the device 60 may transmit a signal (e.g., represented by signal 68) to initially activate the electronics of the injector 10 before use. For example, the processor 52 of the injector 10 may remain in a dormant state until it detects the ready signal received by the interface 58, whereupon the processor 52 may activate the sensor(s) 50 and/or other components of the injector 10 before injection. In addition, the electronic device 60 may receive information from the injector 10 during delivery and present information on the display 62, e.g., in indicator field 66. Alternatively, the injector 10 may include a switch or other actuator (not shown), which may be used to turn the electronics on, e.g., connect the power source 54 to the processor 50 and/or other components of the injector 10. For example, a switch (not shown) may be provided within the distal region 23 or elsewhere within the housing 22 that may be automatically activated when the cartridge 12 is inserted into the distal region 23 to wake-up the electronics of the injector 10 before use.

For example, as best seen in FIG. 5B, a graphical representation or indicator field 66 may be presented on the display 62 indicating one or more of the positions of the piston/plunger, target volume of medicament to be delivered, actual volume of medicament delivered, and the like. In the embodiment shown, a black region 66a on the left side of the indicator 66 may represent an initial position of the plunger 30 of the driver 20, e.g., also corresponding to the initial position of the piston 16 within the syringe cartridge 12 once filled and coupled to the driver 20.

When the actuator 42 of the injector 10 is activated, the plunger 30 and piston 16 begin to displace delivering medicament 6 from the syringe cartridge 12, which may be represented by a different color region 66b being shown on the indicator 66, e.g., initially from the black region towards an opposite end of the indicator 66. In the case of sub-retinal delivery, an initial volume of medicament may be delivered from the syringe cartridge 12, e.g., while the cannula is being advanced towards and/or through the retina. For example, as described further elsewhere herein, initially, the cannula 19 may be directed into an eye 90 (e.g., similar to the device shown in FIG. 1) and positioned adjacent the retina 94, e.g., immediately in front of the retina, using conventional methods.

Once the surgeon is ready to deliver the medicament sub-retinally, the actuator 42 may be activated and then the cannula 19 advanced through the retina 94 while medicament is being delivered. The initial bolus of medicament that is delivered before the retina 94 is pierced is simply released into the interior of the eye 90 and is not considered part of the bleb volume intended to be delivered sub-retinally. In this case, the surgeon may instruct an assistant to activate the activation device 60 immediately upon piercing the retina 94. For example, the assistant may select the "start" icon 64b shown in FIG. 5D, whereupon the device 60 may then communicate a "start" signal to the processor 52 of the injector 10 (via the interface 58), which may begin measuring and/or monitoring the volume of medicament being delivered sub-retinally. Alternatively, a foot switch or other actuator, e.g., a button on the driver (not shown), may be provided that the surgeon may trigger themselves, which may communicate the "start" signal, e.g., when the surgeon steps on or otherwise activates the switch, as described elsewhere herein.

Optionally, the processor 52 may activate the output device(s) to communicate information to the surgeon during delivery. For example, when the actuator 42 of the injector 10 is first activated, the processor 52 may activate the LED 56a to emit yellow light (or other predetermined color) to provide visual confirmation that medicament is being delivered. Once the processor 52 receives the "start" signal, the processor 52 may activate the LED 56a to emit green light (or other predetermined color) to provide visual confirmation that the medicament is being delivered sub-retinally, i.e., to confirm that the volume of the bleb being delivered is now being measured. When a target volume has been delivered, the processor 52 may activate the LED 56a to emit red light (or, again, another predetermined color) to provide visual confirmation that the target volume has been delivered. Alternatively, separate LEDs may be provided that may be activated sequentially to provide the desired visual status indications. In addition or alternatively, a speaker 56b may be activated during each of these stages to emit sounds, e.g., different sounds corresponding to initial delivery, sub-retinal delivery, and achieving the target volume.

If the activation device is a wireless electronic device 60, the assistant may press the "Start" icon (or otherwise interface with the electronic device) to cause the electronic device 60 to communicate the start signal to the processor 52. In this embodiment, the processor 52 may communicate information related to delivery of the medicament 6 back to the electronic device 60 via the communications interface 58, e.g., for presentation on display 62 and/or storage in memory of the device 60. For example, as shown in FIG. 5B, a yellow region 66b may be presented adjacent the black (initial position) region 66a when the actuator 42 is first activated and medicament begins to be delivered (e.g., before piercing the retina). Optionally, the leading edge of the yellow region may translate towards the opposite end of the indicator 66 proportional to the volume delivered, e.g., until the start signal is received.

Once the "start" signal is received by the processor 52, the yellow region 66b may stop, and a green region 66c may begin to translate along the indicator 66 to visually indicate the volume of the bleb delivered sub-retinally. Optionally, a processor of the electronic device 60 may display the target volume on the indicator 66, e.g., as a green outline 66d extending from the yellow region (or black region when the injector is initially activated), e.g., to ensure that the cartridge 12 has sufficient volume to deliver the target volume. In addition or alternatively, the indicator 66 displayed may include graduations or other indicia identifying volume such that the assistant may visually monitor the volume being delivered as the green region passes corresponding indicia on the indicator. When the target volume is achieved, the green region 66c may stop, and a red region (not shown) may begin to translate along the indicator 66, e.g., beyond target volume region 66d, to indicate an excess volume of medicament being delivered. For example, in some applications, a surgeon may decide to deliver additional medicament beyond the original target volume and this volume may be indicated by the red region.

Once the surgeon releases the actuator 42 of the injector 10, delivery may be discontinued and the cannula 19 may be removed from the patient, e.g., similar to conventional methods. After delivery, the injector processor 20 and/or the electronic device 60 may save information related to the delivery for subsequent recording and/or analysis. For example, the volume of pre-bleb medicament released into the eye (the yellow region 66b), the volume of the bleb (the green region 66c and/or red region), and/or other parameters may be saved and used for subsequent analysis and/or treatment of the patient.

Figure 7A:
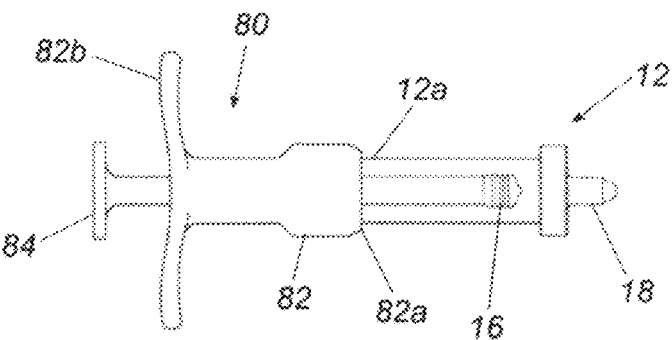
FIGS. 7A-7C are side views showing an exemplary embodiment of a loading device for loading medicament into a syringe cartridge.
Figure 7B:
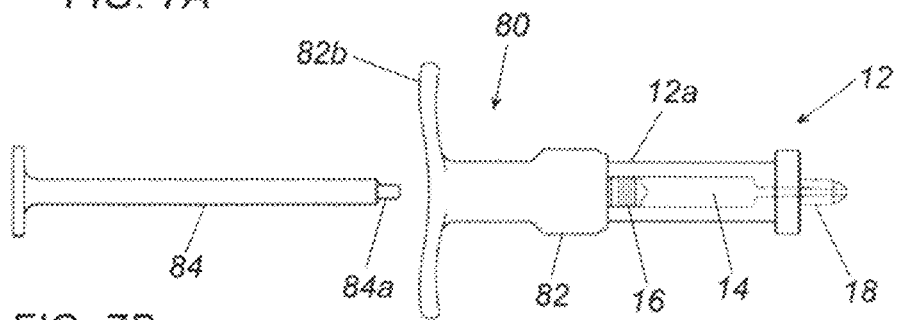
Figure 7C:
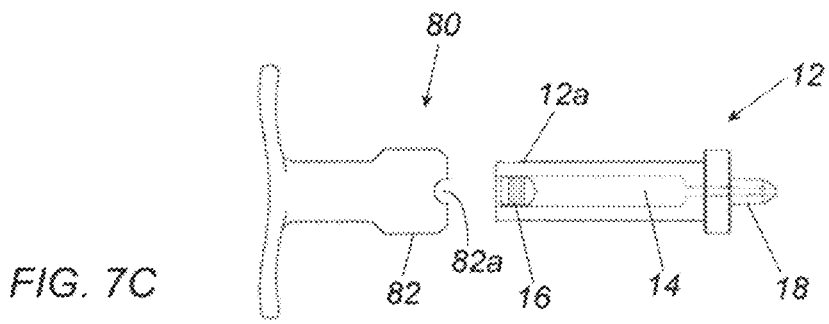

An exemplary method for using the injector shown in FIGS. 2-4 is now described, e.g., for delivering a medicament, such as gene vectors and/or stem cells, sub-retinally 92 within a patient's eye 90, e.g., similar to the device 8 shown in FIG. 1. Initially, a volume of medicament 6 may be loaded into the interior 14 of the syringe cartridge 12 sealed by the piston 16 slidably disposed within the interior 14. For example, as shown in FIG. 7A-7C, the cartridge 12 may be coupled to a loading device or adapter 80, including a housing 82 and a manual plunger 84 that may be used to load medicament (not shown) into the cartridge 12. As shown, the housing 82 includes a tubular body having an open end 82a sized to receive the proximal end 12a of the cartridge 12 therein. Optionally, the housing 82 may include one or more connectors (not shown) for removably securing the cartridge 12 during loading. The manual plunger 84 may be coupled to the piston 16, e.g., by threading a threaded nipple 84a (or engaging another connector, not shown) on the plunger 84 into a similarly threaded recess (or other cooperating connector, not shown) on the piston 16 with the piston 16 in its distal-most position, as shown in FIG. 7A. Once the cartridge 12 is coupled to the loading device 80, a needle cannula, not shown) may be connected to the port 18 of the cartridge 12 and inserted into a container of the medicament (not shown) with the piston 16 in a distal-most position (adjacent the port 18). As shown in FIG. 7B, the manual plunger may be withdrawn to direct the piston 16 proximally away from the port 17, thereby drawing the medicament 6 into the interior 14 as the piston 16 moves proximally. Once sufficiently filled, the cannula may be removed from the container and from the port 18. The plunger 84 may be unthreaded or otherwise disengaged from the piston 16, and the cartridge 12 removed from the loading device 80, as shown in FIG. 7C.

Once the syringe cartridge 12 is filled and/or a desired volume is loaded, the cartridge 12 may be coupled to the driver 20. For example, the cartridge 12 inserted into the distal region 23 of the driver housing 22 until the driver plunger 30 couples to the piston 16. For example, as shown in FIG. 2B, the plunger 30 may include a tab or other connector 35 that may be received in or otherwise engage a recess 17 or other connector on the piston 16. The injector 10 is then ready for delivering the medicament 6 to the patient. Alternatively, it will be appreciated that the separate syringe cartridge may be replaced with an integral syringe region within the driver, which may be prefilled with a desired volume of medicament. In addition, if a needle cannula 19 is not initially provided on the port 18 of the syringe cartridge 12, one may be attached, e.g., using conventional methods, such as a threaded connector, Luer fitting, and the like.

Figure 8A:
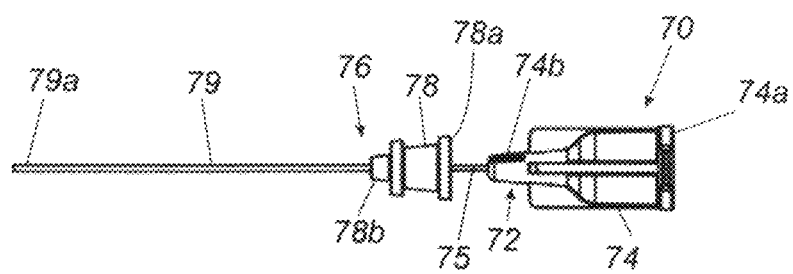
FIGS. 8A and 8B are side views of an exemplary embodiment of a needle cannula that may be attached to a syringe cartridge for delivering medicament from the cartridge.
Figure 8B:
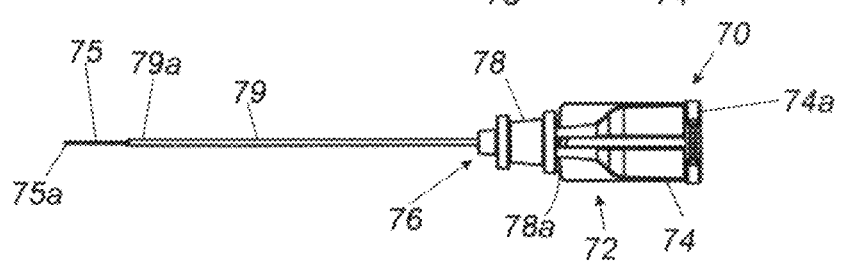

Immediately before delivery, a needle cannula may be connected to the port 18 on the cartridge 12. Turning to FIGS. 8A and 8B, an exemplary embodiment of a cannula assembly 70 is shown that includes an inner injection cannula 72 and an outer protector cannula 76. The inner cannula 72 generally includes a proximal hub 74 including a hollow proximal end 74a sized to be received over and/or otherwise engaged with the port 18 of a cartridge (e.g., such as the cartridge 12 shown in FIGS. 7A-7C or any of the other embodiments herein) and an elongate tubular needle 75 extending from a distal nipple 74b and terminating in a tip 75a, which may be sharpened or blunt depending on the application.

The outer cannula 76 also includes a proximal hub 78 including a hollow proximal end 78a sized to be received over the nipple 74b of the inner cannula hub 74, and a needle 79 extending from a distal nipple 78b. The needles 75, 79 may be formed from stainless steel or other conventional material and the hubs 74, 78 may be formed from plastic or other conventional material, e.g., such that the needles 75, 79 may be bonded or otherwise permanently attached to the respective hubs 74, 78. As shown, the inner needle 75 may be longer than the outer needle 79, e.g., such that the outer needle 79 may be used to protect the inner needle 75 during introduction, and then retracted to expose a tip 75a of the inner needle 75. For example, the assembly 70 may be provided initially with the outer cannula 76 in a distal position, e.g., as shown in FIG. 8A, i.e., with the tip 75a of the inner needle 75 covered by the outer needle 79 and the outer cannula hub 78 spaced apart distally from the inner cannula hub 74. In this configuration, the inner cannula hub 74 may be received over the port 18 of the cartridge 12 to attach the assembly 70 to an injector, such as any of those described herein. During use, the outer needle 79 may remain over the tip 75a of the inner needle 75 during introduction, e.g., to protect the tip 79a. For example, the inner needle 75 may have a very small diameter and relatively thin wall, and so may be fragile, while the outer needle 79 may have a relatively thicker wall and/or greater column strength, which may reduce the risk of bending or breaking the outer needle 79. If the assembly 70 is introduced into a patient's body, e.g., into an eye through a trocar cannula including a septum or valve (not shown), the outer needle 79 may be able to open the septum or valve with minimal risk of damage to advance the inner needle 75 through the trocar cannula.

Once the tip 79a of the outer needle 79 is positioned at a desired location, e.g., within a patient's eye beyond the trocar cannula, the outer cannula 76 may be retracted to expose the tip 75a of the inner needle 75. For example, as shown in FIG. 8B, the outer cannula 76 has been retracted until the outer cannula hub 78 is received over the nipple 74b and/or otherwise engaged with the inner cannula hub 74, thereby preventing subsequent movement of the outer cannula 76, while the tip 75a of the inner needle 75 may then be inserted into a target location for delivering medicament, e.g., as described further elsewhere herein.

Returning to FIGS. 2-4, after attaching a needle or cannula (e.g., cannula 19 or cannula assembly 70) to the cartridge 12, the injector 10 may be ready for use. For example, the actuator lever 42 may be activated to initially activate the driver module 40, e.g., to puncture the gas canister 44 with pin 43, similar to the embodiments described in the applications incorporated by reference herein. Consequently, the gas may be released from the canister 44 to power the fluid plunger 46. Optionally, the actuator 42 may be initially activated to deliver a small bolus of medicament from the cartridge 12, e.g., to fill the cannula 19 and/or otherwise remove air or other potential contaminants. For example, as the lever 42 is actuated (initially and during injection of the medicament 6), a pin 49 may open the fluid passage from the fluid chamber 47 to the plunger housing 48, which may cause incompressible fluid to enter the plunger housing 48 and advance the plunger 30, e.g., at a substantially consistent and uniform translation rate due to the pressure acting on the fluid plunger 46 and fluid entering the plunger housing 48.

If the injector 10 is being used in conjunction with an electronic device, such as device 60 shown in FIGS. 5A and 5B, once this step is completed, a "ready" icon 64a may be selected on the electronic device 60, e.g., to send a ready signal to the injector processor 52 to indicate the initial (zero) position of the plunger 30 and piston 16. This location may be presented on indicator 66 displayed on the electronic device 60 as the black region 66a shown in FIG. 5B.

Similar to the device 8 shown in FIG. 1, the cannula 19 may then be inserted into the patient's eye 90 such that the cannula 19 is disposed adjacent the patient's retina 94, e.g., similar to conventional methods. The actuator lever 42 may then be activated to advance the plunger 30, thereby advancing the piston 16 to deliver medicament 6 from the interior 14 into the patient's eye 90. The processor 52 may monitor the displacement of the plunger 30 based on signals from the sensor(s) 50 and calculate in real time the volume of medicament being delivered into the patient's eye 90.

The cannula 19 may then be advanced to pierce the retina 94 while continuing to deliver medicament, and as this happens, the surgeon can instruct an assistant to activate the activation device 60 (e.g., press the "start" icon 64b on the electronic device's display 62 or activate a stand-alone switch). This action communicates a start signal to the processor 52 and the processor 52 continues to analyze signals from the sensor(s) 50 to monitor further displacement of the plunger 30 and determine the volume of medicament delivered sub-retinally. As described previously, the processor 52 may activate one or more output devices, e.g., an LED 56a and/or speaker 56b, to confirm the status of medicament delivery to the surgeon and/or to communicate information to the electronic device 60 for display 52, e.g., on the indicator 66 shown in FIG. 5B. The surgeon may continue delivery until the target volume is delivered (using the output device 56 and/or electronic device 60) to confirm the volume and, optionally, deliver additional medicament, if desired. Once the desired volume is delivered, the surgeon may release the lever 42 to discontinue delivery and then remove the injector 10, e.g., using conventional methods.

Figure 6A:
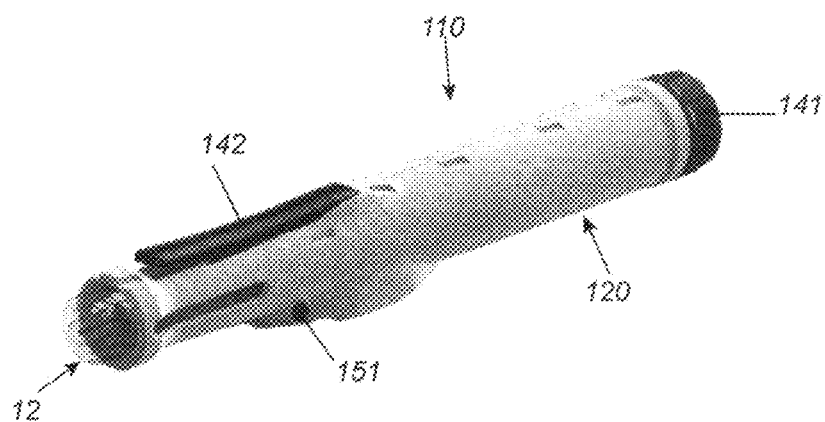
FIGS. 6A and 6B are perspective and cross-sectional views, respectively, of another exemplary embodiment of an injector.
Figure 6B:
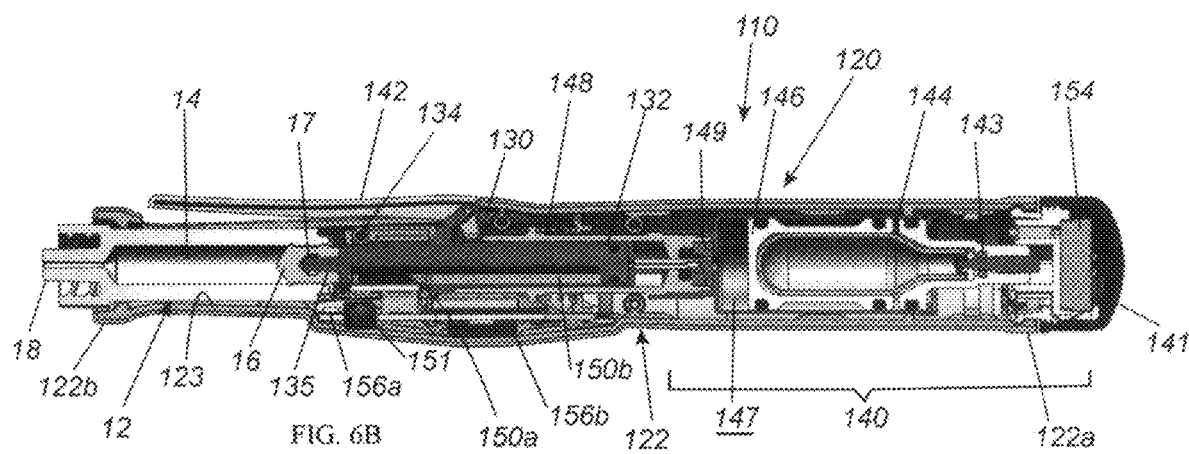

Turning to FIGS. 6A and 6B, another exemplary embodiment of an injector 110 is shown that includes a syringe cartridge 12 and a driver 120, generally similar to the previous embodiments. Similar to the previous embodiments, the cartridge 12 includes a piston 16 slidable within an interior 14 of the cartridge 12, which may be filled with medicament (e.g., preloaded or loaded immediately before use) and an outlet or port 18 to which a cannula (not shown) may be attached before use. When the cartridge 12 is inserted into the distal region 123 of the housing 122, one or more connectors on the cartridge 12 and/or housing 122 may engage to secure the cartridge 12 and, substantially simultaneously, tab 135 (or other connector) on the plunger 130 may engage recess 17 (or other connector) on the piston 16. In addition, a switch (not shown) may be provided that is actuated when the cartridge 12 is inserted, which may activate electronics of the injector 110, as described elsewhere herein.

Also similar to the previous embodiments, the drive module 140 includes a canister of pressurized gas or other high delivery force energy storage device 144, e.g., within a proximal end 122a of the housing 122, which may be opened by a pin 143 during initial activation of the injector 110 to deliver pressurized gas around the canister 144 to apply a distal force to fluid piston 146. Unlike the previous embodiments, in this version, the driver 120 includes an activation cap 141 that may be twisted or otherwise manually actuated to cause the pin 143 to open the canister 144 (rather than using initial actuation of the lever 142, as described elsewhere herein). An incompressible fluid may be provided within fluid chamber 147 beyond the fluid piston 146 that communicates with an interior of plunger chamber 148 such that, upon actuation of the lever 142, pin 149 is displaced to open the fluid path such that the fluid may enter the plunger chamber 148 and advance the plunger 130 distally.

As shown in FIG. 6B, the injector 110 also includes one or more LEDs 156a, e.g., mounted within the housing 122 adjacent an opening or window (not shown) to transmit light out of the housing 122, and a speaker 156b for providing visual and/or audible signals during use of the injector 110, similar to previous embodiments. For example, the LED(s) 156a and speaker 156b may be coupled to a processor (not shown) within the housing 122 that is coupled to a battery 154, communications interface 158 (e.g., including an antenna, not shown for transmitting and/or receiving Bluetooth or other wireless signals), also similar to previous embodiments. In addition, the driver 120 may also include a button, switch, or other "wake-up" actuator (not shown), e.g., within the distal region 123, which may be activated when the cartridge 12 is loaded into the driver 120 to "wake-up" the electrical components of the driver 120, e.g., to connect the battery 154 to the processor and/or other components (e.g., in cases where the injector 110 is used without an activation device).

Unlike the previous embodiments, the injector 110 includes one or more sensors 150 that provide a magnetic tracking device for measuring displacement of the plunger 130. For example, a stationary magnetic sensor 150a may be mounted within the housing 122 adjacent the plunger 130, e.g., immediately adjacent a distal end 134 of the plunger 130. A magnetic strip 150b may be mounted to the plunger that extends at least partially between the distal and proximal ends 134, 132 of the plunger 130. For example, the magnetic strip 150b may be an alternating polarity strip with a desired spacing between the alternating poles along the length of the strip 150b, e.g., having a 1 mm pole spacing. As the plunger 1130 moves axially, causing the strip to move axially past the magnetic sensor 150a, the magnetic sensor 150a may act like an encoder that tracks the axial displacement of the strip 150b. Thus, as the plunger 130 is advanced distally, the magnetic element 150b may pass along the magnetic sensor 150a, and the processor may process the signals that are generated to determine displacement of the plunger 130, e.g., using the known value for the cross-sectional area of the interior 14 of the cartridge 12 to measure the volume of medicament delivered from the injector 110, similar to the previous embodiments).

Also unlike the previous embodiments, the injector 110 includes a "start" button or other actuator 151 on the driver 120, which may be used to communicate a "start" signal to the processor (instead of using a separate activation device), e.g., to measure a dose of medicament being delivered, similar to other embodiments herein.

Generally, the injector 110 may be used similar to the previous embodiments, e.g., to deliver a precise dose of medicament sub-retinally or otherwise into a patient's body. For example, a cartridge 12 may be filled and inserted into the distal region 123 immediately before use, thereby coupling the piston 16 to the plunger 130 and activating the electronics of the injector 110. The cap 141 may then be twisted or otherwise actuated to open the gas canister and power the driver 120 such that subsequent actuation of the lever 142 causes the pressurized fluid to advance the plunger 130, similar to previous embodiments.

The injector 110 is then ready to deliver the medicament, e.g., into a patient's eye (not shown). For example, a cannula (not shown) coupled to the port 18 may be inserted into a patient's eye such that the cannula is disposed adjacent the patient's retina. The actuator lever 142 may then be activated to advance the plunger 130, thereby advancing the piston 116 to begin delivering medicament from the interior 14 into the patient's eye. Optionally, the processor may monitor the displacement of the plunger 130 based on signals from the sensor 150 and calculate in real time the volume of medicament being delivered into the patient's eye.

The cannula may then be advanced to pierce the retina while continuing to deliver medicament, and as this happens, the surgeon can press the "start" button 151, which communicates a start signal to the processor. The processor may continue to analyze signals from the sensor 150 to monitor further displacement of the plunger 130 and determine the volume of medicament delivered sub-retinally. As described previously, the processor may activate one or more output devices, e.g., an LED 156*a* and/or speaker 156*b*, to confirm the status of medicament delivery to the surgeon. For example, the surgeon may continue delivery until the target volume is delivered using the changes in output from the output devices 156 to confirm the volume and, optionally, deliver additional medicament, if desired. Once the desired volume is delivered, the surgeon may release the lever 142 to discontinue delivery and then remove the injector 110, e.g., using conventional methods.

Thus, in this embodiment, the injector may be operated entirely independently from an electronic tablet/smartphone. The processor may record data, e.g., related to volume of medicament delivered and/or other information, in onboard memory (not shown), which may be retrieved later, e.g., by communicating with an external electronic device using the communications interface 158, e.g., to connect via Bluetooth or other protocols to download the information.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

It will also be appreciated that elements or components shown with any embodiment herein are exemplary for the specific embodiment and may be used on or in combination with other embodiments disclosed herein.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An injector device for delivering a medicament into a patient's body, comprising:
   a syringe cartridge comprising a housing including a proximal end, a distal end, and defining an interior, the cartridge further comprising a piston slidably disposed within the interior for delivering the medicament within the interior through an outlet in the distal end;
   a syringe driver comprising a plunger for advancing the piston within the interior of the housing, a source of pressurized fluid, and an actuator member for opening a flow path at least partially between the source and the plunger to advance the plunger and the piston to deliver the medicament from the interior of the housing;
   one or more sensors operatively coupled to the plunger to measure displacement of the plunger;
   a processor coupled to the one or more sensors for analyzing signals from the one or more sensors to measure a volume of medicament delivered from the outlet based at least in part on the displacement of the plunger; and
   an output device coupled to the processor for providing one or more outputs related to the volume of medicament delivered from the outlet,
   wherein the cartridge is removably received within a distal region of an outer housing of the driver such that the outlet is oriented distally relative to the driver, and
   wherein the piston and plunger comprise one or more connectors that couple the piston to the plunger when the cartridge is received within the distal region.

2. The device of claim 1, wherein the output device comprises a light source coupled to the processor and configured to provide visible indications related to activation and operation of the device.

3. The device of claim 2, wherein the light source comprises a multiple-color LED configured to emit a first color to indicate when medicament is initially delivered from the cartridge, and a second color when the processor receives a start signal to indicate when medicament is being delivered to a target location.

4. The device of claim 3, wherein the multiple-color LED is configured to emit a third color when the processor confirms that a predetermined dose has been delivered to the target location.

5. The device of claim 1, wherein the output device comprises a speaker coupled to the processor and configured to provide audible indications related to activation and operation of the device.

6. The device of claim 1, wherein the one or more sensors comprise one or more optical sensors mounted within the housing adjacent the plunger to generate signals related to the displacement of the plunger.

7. The device of claim 6, wherein the one or more optical sensors are mounted concentrically around the plunger.

8. The device of claim 1, wherein the one or more sensors comprise a magnetic sensor mounted within the housing adjacent the plunger to generate signals related to the displacement of the plunger.

9. The device of claim 8, further comprising an alternating polarity magnetic strip on the plunger configured to generate the signals as each pole of the strip passes the magnetic sensor to track the displacement of the plunger.

10. The device of claim 1, wherein the cartridge is removably coupled to a housing of the driver.

11. The device of claim 10, further comprising a switch that is actuated when the cartridge is coupled to the housing to deliver power from a power source to the processor.

12. The device of claim 1, wherein the cartridge is removably received within a distal region of an outer housing of the driver such that the outlet port is oriented distally relative to the driver.

13. The device of claim 1, further comprising a switch on the driver that is coupled to the processor to deliver a "start" signal when actuated, whereupon the processor analyzes signals from the one or more sensors to measure the volume of medicament delivered from the outlet.

14. The device of claim 1, further comprising memory communicating with the processor for storing data comprising information related to the medicament delivered from the outlet.

15. The device of claim 14, wherein the processor is configured to determine one or more of the following data for storing in the memory based at least in part on the signals: total volume of the medicament delivered from the interior, total volume delivered into a target location, volume rate of the medicament delivered from the interior, and dosing profile of the medicament delivered from the interior.

16. The device of claim 1, wherein the one or more connectors comprise a tab on the plunger and a recess on the piston.

17. An injector device for delivering a medicament into a patient's body, comprising:
- a syringe cartridge comprising a housing including a proximal end, a distal end, and defining an interior, the cartridge further comprising a piston slidably disposed within the interior for delivering the medicament within the interior through an outlet in the distal end;
- a syringe driver comprising a plunger for advancing the piston within the interior of the housing, a source of pressurized fluid, and an actuator member for opening a flow path at least partially between the source and the plunger to advance the plunger and the piston to deliver the medicament from the interior of the housing;
- one or more sensors operatively coupled to the plunger to measure displacement of the plunger;
- a processor coupled to the one or more sensors for analyzing signals from the one or more sensors to measure a volume of medicament delivered from the outlet based at least in part on the displacement of the plunger;
- an output device coupled to the processor for providing one or more outputs related to the volume of medicament delivered from the outlet; and
- a communications interface coupled to the processor for receiving wireless signals from an activation device, the processor configured to identify a "ready" signal from the wireless signals to activate the device from a dormant state.

18. The device of claim 17, wherein the processor is further configured to identify a "start" signal from the wireless signals, whereupon the processor analyzes signals from the one or more sensors to measure the volume of medicament delivered from the outlet.

19. An injector device for delivering a medicament into a patient's body, comprising: a syringe cartridge comprising a housing including a proximal end, a distal end, and defining an interior, the cartridge further comprising a piston slidably disposed within the interior for delivering the medicament within the interior through an outlet in the distal end; a syringe driver comprising a plunger for advancing the piston within the interior of the housing, a source of pressurized fluid, and an actuator member for opening a flow path at least partially between the source and the plunger to advance the plunger and the piston to deliver the medicament from the interior of the housing; one or more sensors operatively coupled to the plunger to measure displacement of the plunger; a processor coupled to the one or more sensors for analyzing signals from the one or more sensors to measure a volume of medicament delivered from the outlet based at least in part on the displacement of the plunger; and an output device coupled to the processor for providing one or more outputs related to the volume of medicament delivered from the outlet, wherein the cartridge is removably received within a distal region of an outer housing of the driver such that the outlet is oriented distally relative to the driver, and wherein the cartridge housing and the driver comprise one or more cooperating connectors that secure the cartridge within the distal region.

20. An injector device for delivering a medicament into a patient's body, comprising:
- a syringe cartridge comprising a housing including a proximal end, a distal end, and defining an interior, the cartridge further comprising a piston slidably disposed within the interior for delivering the medicament within the interior through an outlet in the distal end;
- a syringe driver comprising a plunger for advancing the piston within the interior of the housing, a source of pressurized fluid, and an actuator member for opening a flow path at least partially between the source and the plunger to advance the plunger and the piston to deliver the medicament from the interior of the housing;
- one or more sensors operatively coupled to the plunger to measure displacement of the plunger;
- a processor coupled to the one or more sensors for analyzing signals from the one or more sensors to measure a volume of medicament delivered from the outlet based at least in part on the displacement of the plunger; and
- an output device coupled to the processor for providing one or more outputs related to the volume of medicament delivered from the outlet,
- wherein the cartridge housing is permanently coupled to the driver.

21. A system for delivering a medicament into a patient's body, comprising:
- an injector device comprising:
  a) a syringe cartridge comprising a housing defining an interior and a piston slidably disposed within the interior for delivering the medicament within the interior through a distal outlet in the housing;
  b) a syringe driver comprising a plunger coupled to the piston, a driver module, and an actuator member for delivering pressurized fluid within the driver module to advance the plunger and the piston to deliver the medicament from the interior of the housing;
  c) one or more sensors operatively coupled to the plunger to measure displacement of the plunger;

d) a processor coupled to the one or more sensors for analyzing signals from the one or more sensors to measure a volume of medicament delivered from the outlet;

e) one or more output devices coupled to the processor for providing one or more outputs related to the volume of medicament delivered from the outlet and f) an injector communication interface; and an electronic device comprising:

a) a device communication interface for transmitting signals to and receiving signals from the injector communication interface;

b) a user interface for entering a "start" signal for transmission to the processor, whereupon the processor analyzes signals from the one or more sensors to measure the volume of medicament delivered; and c) a display for presenting an indicator field including information regarding the volume of medicament delivered from the outlet received in signals from the processor.

22. An injector device for delivering a medicament into a patient's body, comprising: a syringe cartridge comprising a housing including a proximal end, a distal end, and defining an interior, the cartridge further comprising a piston slidably disposed within the interior for delivering the medicament within the interior through an outlet in the distal end; a syringe driver comprising a plunger for advancing the piston within the interior of the housing, a source of pressurized fluid, and an actuator member for opening a flow path at least partially between the source and the plunger to advance the plunger and the piston to deliver the medicament from the interior of the housing; one or more sensors operatively coupled to the plunger to measure displacement of the plunger; a processor coupled to the one or more sensors for analyzing signals from the one or more sensors to measure a volume of medicament delivered from the outlet based at least in part on the displacement of the plunger; an output device coupled to the processor for providing one or more outputs related to the volume of medicament delivered from the outlet; an activation device; and an injector communications interface within the housing for receiving a "start" signal from the activation device, whereupon the processor analyzes signals from the one or more sensors to measure the volume of medicament delivered.

23. The device of claim 22, wherein the activation device comprises a switch that is actuatable to communicate the "start" signal to the processor.

24. The device of claim 22, wherein the injector communications interface is configured to transmit and receive signals wirelessly.

25. The device of claim 24, wherein the activation device comprises an electronic device comprising a communications interface for communicating with the injector via the injector communications interface, and a display for presenting information related to delivery of the medicament.

26. An injector device for delivering a medicament into a patient's body, comprising:

a syringe cartridge comprising a housing defining an interior, the cartridge further comprising a piston slidably disposed within the interior for delivering the medicament within the interior through an outlet in a distal end of the housing;

a syringe driver comprising a plunger for advancing the piston within the interior of the housing, a source of pressurized fluid, and an actuator member for opening a flow path at least partially between the source and the plunger to advance the plunger and the piston to deliver the medicament from the interior of the housing;

one or more sensors operatively coupled to the plunger to measure displacement of the plunger;

a processor coupled to the one or more sensors for analyzing signals from the one or more sensors to measure a volume of medicament delivered from the outlet based at least in part on the displacement of the plunger;

a start actuator coupled to the processor; and one or more light sources coupled to the processor, the processor configured to activate the one or more light sources to:

a) emit a first color when the actuator member is initially actuated to begin delivering medicament from the cartridge, b) emit a second color when the processor detects that the start actuator has been actuated to indicate when medicament is being delivered to a target location, at which time the processor begins to measure the volume of medicament being delivered to the target location based at least in part on the signals, and c) emit a third color when the processor confirms that a predetermined dose of the medicament has been delivered to the target location.

\* \* \* \* \*